United States Patent [19]
Anderson

[11] Patent Number: 5,817,028
[45] Date of Patent: Oct. 6, 1998

[54] METHOD AND DEVICE FOR THE PROVOCATION OF AIR PASSAGE NARROWING AND/OR THE INDUCTION OF SPUTUM

[75] Inventor: Sandra Doreen Anderson, Birchgrove, Australia

[73] Assignee: Central Sydney Area Health Service, Camperdown, Australia

[21] Appl. No.: 696,987

[22] PCT Filed: Feb. 23, 1995

[86] PCT No.: PCT/AU95/00086

§ 371 Date: Nov. 4, 1996

§ 102(e) Date: Nov. 4, 1996

[87] PCT Pub. No.: WO95/22993

PCT Pub. Date: Aug. 31, 1995

[30] Foreign Application Priority Data

Feb. 25, 1994 [AU] Australia ................................. PM4114

[51] Int. Cl.⁶ .................................................. A61M 11/00
[52] U.S. Cl. ................ 600/529; 128/200.14; 128/200.23
[58] Field of Search .................................. 128/716, 725, 128/724, 720, 200.14, 200.23, 200.24, 200.25; 600/3, 529, 533, 537, 535

[56] References Cited

U.S. PATENT DOCUMENTS

| | | | |
|---|---|---|---|
| 4,446,862 | 5/1984 | Baum et al. | 128/203.15 |
| 5,320,108 | 6/1994 | Cloutier | 128/203.15 |
| 5,497,763 | 3/1996 | Lloyd et al. | 128/200.14 |
| 5,507,277 | 4/1996 | Rudsamen et al. | 128/200.14 |
| 5,509,404 | 4/1996 | Lloyd et al. | 128/200.14 |
| 5,522,385 | 6/1996 | Lloyd et al. | 128/200.14 |
| 5,544,646 | 8/1996 | Lloyd et al. | 128/200.14 |
| 5,558,085 | 9/1996 | Rudsamen et al. | 128/200.14 |
| 5,642,728 | 7/1997 | Andersson et al. | 128/203.15 |
| 5,660,166 | 8/1997 | Lloyd et al. | 128/200.14 |

FOREIGN PATENT DOCUMENTS

| | | |
|---|---|---|
| 1297012 | 12/1991 | Canada . |
| 177783 | 4/1992 | European Pat. Off. . |
| 3518665835 | 11/1988 | Germany . |
| 2055046 | 11/1979 | United Kingdom . |
| WO87/05213 | 3/1983 | WIPO . |
| WO91/11179 | 2/1987 | WIPO . |
| WO94/17822 | 2/1994 | WIPO . |

OTHER PUBLICATIONS

European Journal of Respiratory Diseases, vol. 66(2), 1985, B.G. Simonsson et al., Acute and long–term airway hyperactivity in aluminum–salt exposed workers with nocturnal asthma.

*Primary Examiner*—Max Hindenburg
*Assistant Examiner*—Stephen Huane
*Attorney, Agent, or Firm*—Rockey, Milnamow & Katz, Ltd.

[57] ABSTRACT

A method as described for testing the susceptibility of a person to asthma. The person inhales an effective amount of sodium chloride, mannitol or another substance capable of altering the osmolarity of airway surface liquid in the subject. The substance is in the form of a dispersible dry powder containing an effective proportion of particles of a respirable size. The subject is then measured to detect airway narrowing which is indicative of a propensity for asthma. The same technique of dry powder inhalation can be used to test for the susceptibility of a person to rhinitus, to induce sputum and promote mucociliary clearance.

21 Claims, 4 Drawing Sheets

% PREDICTED FEV₁ PRE- and POST CHALLENGE

METHOD AND DEVICE FOR THE PROVOCATION OF AIR PASSAGE NARROWING AND/OR THE INDUCTION OF SPUTUM

FIELD OF THE INVENTION

The present invention relates to a method and device useful to provoke airway narrowing and/or the induction of sputum. More particularly the invention relates to the use of dry powdered substances to induce a change in the osmolarity of the airways to induce narrowing and/or the induction of sputum.

BACKGROUND ART

Asthma is a chronic inflammatory disease of the airways resulting in bronchial hyperresponsiveness to a wide variety of chemical, physical, and allergenic stimuli. This sensitivity is manifested by narrowing of the airways and a reduction in the forced expiratory volume in one second ($FEV_1$). Bronchial provocation testing, measuring changes in $FEV_1$ in response to inhaled stimuli, is well established as a technique for identifying and assessing the severity of airway hyperresponsiveness in persons suspected of having asthma (J Allergy Clin Immunol 1979; 64:1–250, Sterk et al Eur Respir J 1993,6(Supp 16):53–83. The most commonly used provocative agents are histamine and methacholine that act directly on specific receptors in the airways causing bronchial smooth muscle contraction. Challenges with these agents have a high negative predictive value but a low specificity for asthma when performed in a random population. Recently there have been problems with availability of these agents and accreditation for their use in humans. Currently the only product approved for human use by the Federal Drug Administration in the USA is Provoline (Hoffman La Roche) which is methacholine chloride.

Bronchial provocation testing with dry powders containing respirable particles of allergens (e.g. flour, red cedar wood dust, resins, gums) has also been used to identify specific allergens in order to establish a relationship between exposure to the suspected agent and the onset of asthma. These are most commonly used to investigate occupational asthma.

In the last 10 years the inventor's laboratory has developed and standardised a bronchial provocation test using wet aerosols of hyperosmolar saline generated by an ultrasonic nebuliser (Anderson et al., in Provocation Testing in Clinical Practice, pp 249–278, Marcel Dekker Inc. 1994). This test is now well established in Laboratories throughout Australia and is listed in the Medical Benefits Schedule Book. This challenge test is also included in the report of the working party of the European Community for Steel and Coal (Sterk et al., Eur Respir J, 1993,6(Supp 16):53–83). It has recently been recommended by the Bronchial Provocation Committee of the International Study of Asthma and Allergy in Children.

Hyperosmolar saline challenge appears to be a very useful technique to identify persons with current asthma and those who suffer exercise-induced asthma. It is also very useful to evaluate the drugs used in the treatment of asthma.

The major disadvantage of using wet aerosols of hyperosmolar saline is that an ultrasonic nebuliser is required and this is expensive. Another disadvantage is that ultrasonic nebulisers require maintenance for cleaning and sterilisation. Further a weighing machine is required to measure the output for each test as the nebulisers differ in output over time and between machines. Another disadvantage, as with other wet aerosols, is that the person administering the challenge is also exposed to the aerosol as more than half of the amount generated by the nebuliser is expelled into the environment. Further the personnel are also exposed to saliva from the patient. There are also some difficulties encountered by the patient and these include the use of a nose peg, the production of a lot of saliva and the taste of salt. The time taken to perform the challenge with a wet aerosol in a mild asthmatic or healthy control maybe 70 minutes. This comprises preparation of solution and apparatus (about 10 minutes), actual challenge time which for mild asthmatics may be up to 30 minutes, and finally post challenge cleaning and sterilisation (about 30 minutes).

It is also known that wet aerosols of salt can be used for the purpose of increasing mucociliary clearance and inducing sputum in a subject. This technique has been used since the 1970's by physiotherapists to enhance the clearance of secretions from the airways of subjects having cystic fibrosis and bronchitis. In recent years the technique has been used with patients with HIV who are suspected of having *Pneumocystis carinii* which causes pneumonia and needs to be treated. Sputum analysis in patients suspected of having tuberculosis is also known as a simple technique to look for the disease.

By increasing the osmolarity of the airway surface liquid, water moves towards the lumen of the airway. This movement of water and the increased mucociliary clearance induced by hyperosmolarity also stimulates sputum production. The problem associated with this treatment is similar to the problem associated with the hyperosmolar saline challenge for the determination of airway narrowing. An expensive nebuliser is required to carry out the procedure.

BRIEF DISCLOSURE OF THE INVENTION

The present invention consists in a method for attempting to provoke airway narrowing in a subject comprising the steps of (a) causing the subject to inhale into the airways an effective amount of a substance capable of altering the osmolarity of airway surface liquid in the subject, which substance is in the form of a dispersible dry powder containing an effective proportion of particles of a respirable size, and (b) measuring in the subject a parameter indicative of the resistance to air flow of the subject's airways.

In another aspect the present invention consists in a method for inducing sputum comprising the step of causing a subject to inhale into his or her airways an effective amount of a substance capable of altering the osmolarity of airway surface liquid, the substance being in the form of a dispersible dry powder containing an effective proportion of particles of a respirable size.

In a still further aspect the present invention consists in a rupturable container containing an effective quantity of a substance capable of altering the osmolarity of airway surface liquid in a subject, the substance being in the form of a dispersible dry powder containing an effective proportion of particles of a respirable size.

The administration of a hyperosomolar challenge to a subject in the form of a dry powder rather than a wet aerosol enables the challenge to be administered through a conventional dry powder inhaler rather than through a nebuliser. This is highly advantageous as these inhalers are very cheap and are widely available. The time to perform a challenge is halved as there is no cleaning, sterilising, maintenance or weighing involved in the use of the dry powder test. It would also appear that smaller doses of challenge substance need to be administered in the dry state to achieve a desired response than was required with that substance in the form of a wet aerosol.

As used in this specification, the term "airways" includes both the upper airways of the nose and the lower airways of the lungs. While the invention is particularly applicable in the latter case it is also applicable in the former case for the detection of actual or incipient rhinitis, which may be due to dry air or allergens, and similar conditions. While the invention is hereinafter described with particular reference to the lower airways, this teaching could be applied with equal effect to the airways of the nose.

The substance to be inhaled may be any substance that is biologically compatible with the subject and is capable of altering, normally increasing, the osmolarity of the airway surface liquid of the subject. Preferably the substance is a mineral salt or a sugar or sugar alcohol, more preferably it is selected from the group comprising salts of sodium or potassium, hexose and pentose sugars and their corresponding sugar alcohols. It is most preferred that the substance is selected from the group comprising sodium chloride, potassium chloride, mannitol and dextrose. Of the more preferred groups of substances sodium chloride and mannitol are the most preferred for their cheapness, their availability in the required particle size and their biological compatibility.

The substance is required to be inhaled into the airways, usually the first 8–12 generations, and an effective quantity is required to deposit on the surface of the airways. Preferably the substance will make contact with the airways surface in the first twelve generations of the airways. For this to happen it is necessary for the inhaled substance to be present initially in a sufficient quantity, for it to be sufficiently dispersible that it can be entrained by the subject's inhaled breath or by a propellant gas, and a sufficient proportion must be of a respirable particle size. The term "respirable particle size" is taken to mean a size that is sufficiently small that the particle will not settle out or impact against the subject's throat rather than be drawn into the airways of the subject's lungs. In practice it has been found that particles of less than about seven microns are respirable.

In the case in which it is desired to induce airway narrowing, such as for testing for asthma, it may be desirable that as much of the powder is of a respirable size as is possible to reduce impaction on the oropharynx. In this case particles in the respirable range preferably comprise at least 10% of the substance by weight, more preferably at least 25%, even more preferably at least 40% and most preferably at least 50%. By contrast in the case where it is desired to induce sputum it may be desirable to include both respirable particles and non-respirable particles as the latter may induce coughing which will itself assist in the production of sputum. The desired dose in either case will depend upon individual circumstances and will be selected by the supervising health care personnel.

The method for attempting to provoke narrowing may be used for testing subjects for their susceptibility to asthma. In this case the subject may be administered a series of challenges each of a higher dose of the selected substance. After each challenge the subject will be tested for airway narrowing, usually by measuring the forced expiratory volume in 1 second ($FEV_1$). Other known methods for measuring parameters indicative of airway narrowing could equally well be used and airway resistance is usually used for the nose. It will be appreciated that in many cases there will be no narrowing which is indicative of a negative propensity for asthma or rhinitis. In the case of subjects susceptible to asthma there will be a narrowing of the airways proportional to the sensitivity of the subject to the effective administered dose of the substance, that is the dose actually reaching the airway surface. In each case the parameter indicative of resistance to airflow after challenge is compared with the same parameter measured before the challenge to indicate the presence or absence of airway narrowing.

The substance is preferably packaged in a rupturable hard capsule, e.g. gelatin. The capsules preferably contain doses of from 1 to 100 mg, preferably 5 to 40 mg in the case of challenge testing for asthma or rhinitis. In the case of sputum induction and mucocilliary clearance, higher doses may prove desirable in subjects where airway narrowing is not a concern. In the case where it is desired to induce sputum from asthmatics or increase mucociliary clearance it may be necessary to premedicate the subject with a beta adrenoreceptor agonist, Intal or Nedocromil sodium before treatment to prevent the airways narrowing.

The present method for the induction of sputum may be used not only to collect sputum for analysis for the presence of viral or microbial pathogens but also in asthmatics to harvest inflammatory cells from the lung. This allows the state of activation of these inflammatory cells to be determined without invasive harvesting of the cells from the subject.

BEST METHOD OF CARRYING OUT THE INVENTION AIM

Figure 1:
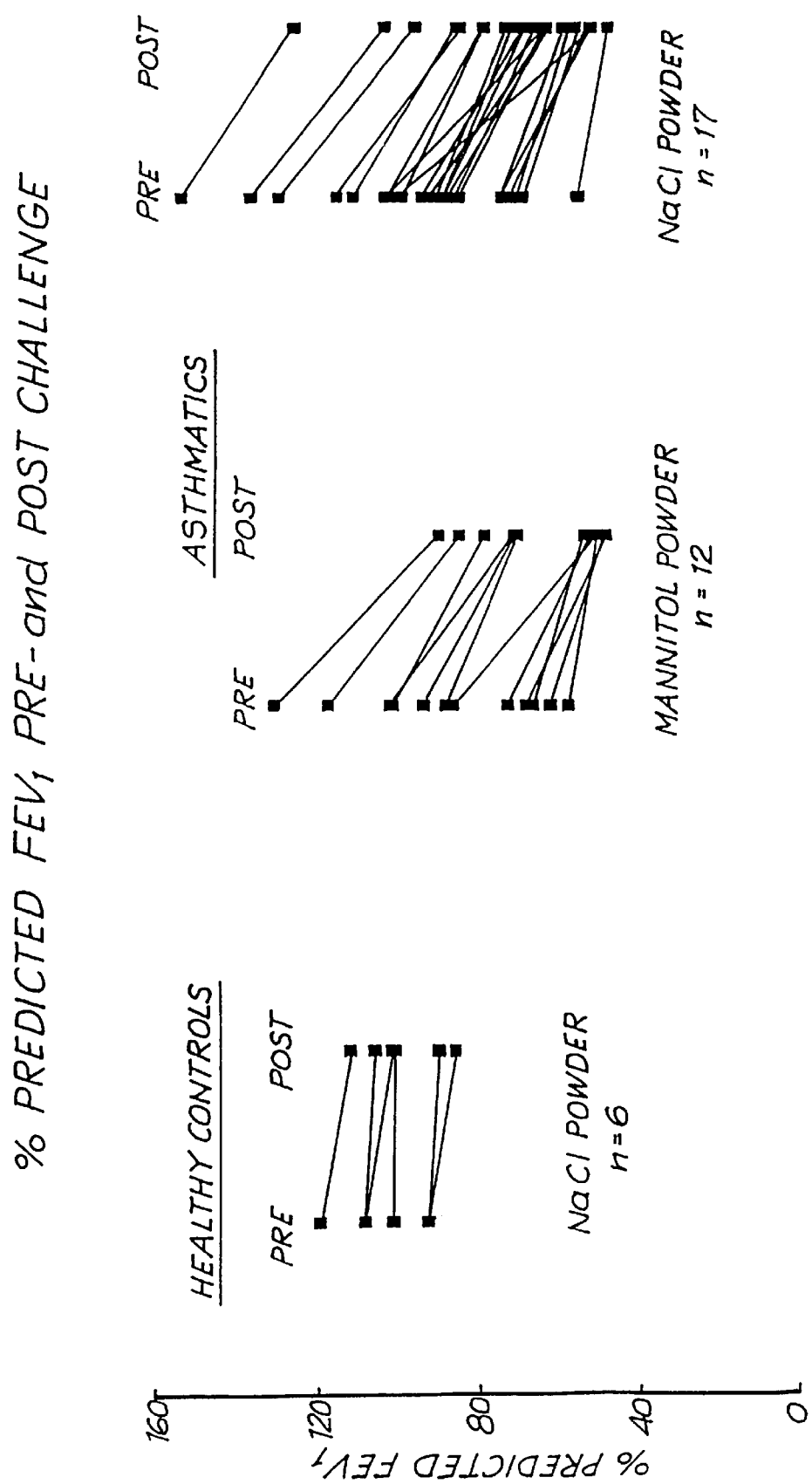
FIG. 1 is a graph showing the percentage of predicted $FEV_1$ for healthy and asthmatic subjects before and after a dry powder challenge according to the present invention.

To establish the efficacy of using a capsule system to deliver sodium chloride or mannitol particles for inducing airway narrowing in patients being treated for asthma.

SUBJECTS

Asthmatics born between Jun30, 1951 and Aug19, 1975 aged between 19–55 years were recruited from the local community. All were clinically recognised asthmatics and were being treated for this disease. All subjects were non-smokers, had a baseline forced expiratory volume in one second ($FEV_1$) greater than 50% and a provocation dose of 4.5% saline to cause a 20% fall in $FEV_1(PD_{20})<30$ ml.

The protocol for the 4.5% saline challenge was that described by Rodwell et al 1992, (American Review of Respiratory Disease, 1992; 146:1149–55). Subjects were excluded from the study if they had a chest infection in the previous six weeks. Subjects could not take bronchodilators for six hours before the lab visit, no corticosteroids were taken on the day of the study and no anti-histamines for three-five days before the study day.

This study was approved by the Royal Prince Alfred Hospital Ethics Committee and all subjects were required to sign a consent form prior to commencing the study. The study was performed under the Clinical Trial Notification Scheme (CTN No 94–492,94–633) of the Therapeutics Goods Administration of the Commonwealth Department of Health of Australia.

METHOD

Experimental design

On the first visit to the laboratory each subject performed a standard hyperosmolar saline challenge with 4.5% saline delivered by an ultrasonic nebuliser. They were included in the study if they had a 20% reduction in $FEV_1$ provoked by this challenge. An asthmatic response is considered to be a reduction in $FEV_1$ greater than 15% from the pre-challenge value. They returned to the laboratory on 2 to 5 occasions. A minimum period of 48 hours separated each visit. On at least one of these occasions they inhaled an encapsulated dry powder of either sodium chloride or mannitol. Seventeen subjects performed the challenge with sodium chloride using a Halermatic(Fisons Pharmaceuticals)(Experiment 1), thirteen subjects performed a challenge with mannitol (Experiment 2) and 10 of these same subjects also performed a challenge with dry sodium chloride (Experiment 3) using a Ingelheim Inhalator (Boehringer Ingelheim).

Preparation and device for delivering powder

Dry powder of sodium chloride or mannitol were prepared by spray drying an aqueous solution and milling, if necessary, so that particle size was in the respirable range (<7 microns). The powder was produced by Genentech Inc, South San Francisco, Calif. and sent in vials of 400 or 600 mg to our laboratory. There were two batches of sodium chloride and one of mannitol. Gravimetrically determined (change from known, known may be preferable) amounts (5, 10, 20 and 40 mg) of the dried powder were packaged in hard gelatin capsules (Gallipot, St Paul, Minn. 55120) by our laboratory staff. In order to reduce any possibility of re-hydration, this was carried out under controlled air conditions (temperature 16°–20° C. relative humidity 40%).

Delivery of the powder to the subjects

Either the Halermatic or Ingelheim Inhalator was loaded with a capsule containing either 5, 10, 20, or 40 mg of sodium chloride or mannitol. The capsule was broken and the subject inhaled either once or twice to empty the capsule.

Measurement of flow rates

The inspiratory flow rate through the Halermatic was measured indirectly by measuring the change in pressure at the mouth ( Viggo-Spectromed DTX Disposable Pressure Transducer, Oxnard, Calif., USA) during a maximal forced inspiration and values between 29–188 L/min were recorded (Miniwriter Type WTR771A, Watanabe Instruments Corp). The low flow rates are due to the resistance of the device. For the Ingelheim Inhalator the inspiratory flow rate was measured by attaching it to a Minato Autospirometer (AS 800, Osaka, Japan) with the subject being asked to perform a maximum inspiratory manoeuvre through an empty Ingelheim Inhalator at the beginning of each study day. The Minato AS 800 was calibrated using a rotameter and variable flow.

Measurement of the response

The $FEV_1$ was measured (Minato Autospirometer AS300, Minato Medical Science Co Ltd, Osaka, Japan) in duplicate, 60 seconds after the administration of the capsule.

The highest value was taken to calculate the airway response.

The reduction in $FEV_1$ for each dose was expressed as a percentage of the value for $FEV_1$ measured 60 seconds after an inhalation manoeuvre had been made from the inhaler containing an empty capsule.

The challenge was started by giving an empty capsule. The dose was started at 5 mg and was doubled with each exposure to a cumulative dose of 635 mg (5, 10, 20, 40, 2×40, 4×40, 4×40, 4×40 mg). This protocol for dosing was varied by repeating the same dose if the subject had a 'significant' reduction in FEV1.

The subjects performed spirometry for at least 30 minutes following the completion of each challenge to assess spontaneous recovery.

The airway response has been expressed in terms of the dose delivered that was required to provoke a 20% reduction in FEV1 ($PD_{20}$). A value for a 15% fall in FEV1 could equally have been used ($PD_{15}$). These values were obtained by linear interpolation from a graph relating % fall in $FEV_1$ to the dose of sodium chloride or mannitol delivered.

Measurement of the particle size

The particle size was measured on a multistage liquid impinger (Astra Pharmaceuticals). This device measures particles in the range of 13–6.8 mm, 6.8–3.1 mm and <3.1 mm. This device was used to measure the dose of sodium chloride that was in the respirable range (<6.8 mm). To do this 25 ml of sodium chloride or mannitol of known osmolarity was placed in each of the 3 stages of the impinger. Three 40 mg capsules of sodium chloride or mannitol were placed in either the Halermatic or an Inhalator and the powder was drawn, by a vacuum pump, through the impinger via a 'throat' at 60 L/min. The osmolarity of the fluid in the 3 stages was measured. The results of this showed that for the sodium chloride delivered by the Halermatic approximately 30% was within the respirable range. For the mannitol via the Ingelheim Inhalator it was 22% and for the sodium chloride via the Inhalator it was 16%.

STATISTICS

The geometric mean and 95% confidence intervals have been calculated for the $PD_{20}$ for the wet aerosol challenge with 4.5% saline and the dry powder challenge with sodium chloride and mannitol. A paired t-test was carried out after log transformation of the values. Pre-challenge lung function ($FEV_1$) was also compared using a paired t-test. The relationship between the $PD_{20}$ to dry mannitol and sodium chloride and wet 4.5% saline was determined using a Piersons correlation coefficient. A value of $p<0.05$ was taken as significant.

Reference values

For spirometry were taken from either Goldman & Becklake (Am Rev Respir Dis 1956;79:457–467) or for the studies with the Ingelheim Inhalator from Quanjer et al (Eur Resp J 1993; 6(Supp 16)5–40). Reference values for normal responses to 4.5% saline are taken from Smith & Anderson (Eur Respir J 1990; 3:144–151). The upper limit of the fall in $FEV_1$ in healthy control subjects is 12%.

Asthmatic subjects

Figure 2:
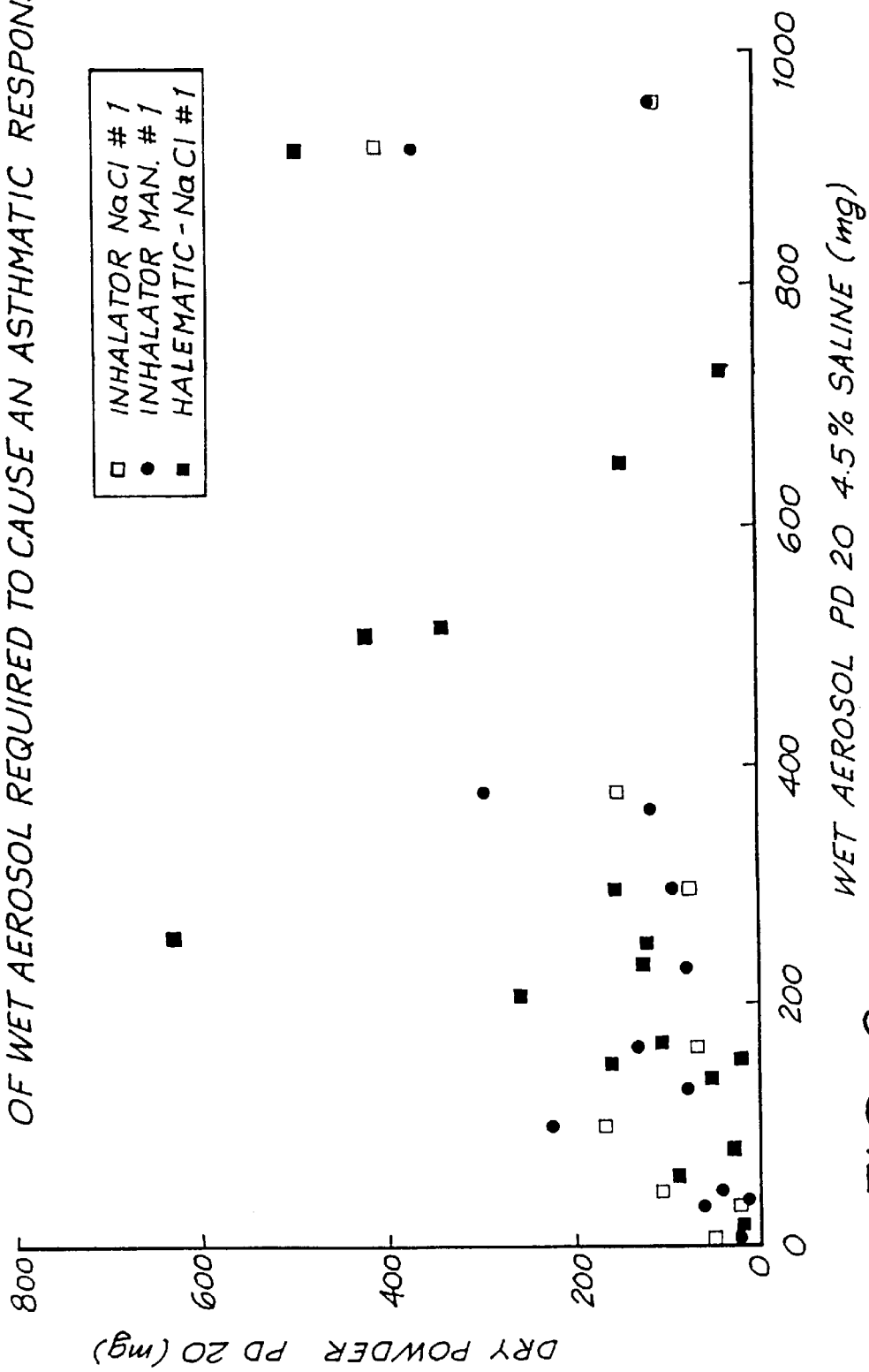
FIG. 2 is a graph showing the dose of dry powder relative to the dose of wet aerosol required to cause an asthmatic response in susceptible subjects.

The results are presented in the three accompanying tables and illustrated in FIGS. 1 & 2 for all tests. The asthmatic medication currently being used by the subjects, the $FEV_1$ as a percentage of the predicted value on the initial visit (control day), the $PD_{20}$ values for the challenge with the wet aerosol of 4.5% saline, the dry powder of mannitol or sodium chloride are given in Tables 1–3 for all subjects. For many subjects a second challenge was performed with the dry powder to demonstrate reproducibility of the airway response. For one study some of the subjects also performed a challenge test using methacholine and the $PD_{20}$ values for these subjects are also given in Table 2. There was no significant difference between the pre-challenge values for FEV1 on each study day or the $PD_{20}$ provoked by the capsule on two test days for any of the experiments.

FIG. 1 illustrates, for each test, the pre and end challenge values for $FEV_1$ expressed as a percentage of the predicted normal value. This demonstrates clearly that the airway response to the dry powder challenge was different between the healthy control subjects and the asthmatic subjects and that the airways of the asthmatic subjects narrowed in response to inhaling the dry powders (in all but one case). FIG. 2 illustrates the $PD_{20}$ to the dry powders of sodium chloride and mannitol in relation to the wet aerosol of 4.5% saline. This demonstrates that the subjects were somewhat more sensitive to the inhalation of the dry powders of sodium chloride and mannitol, compared with the wet aerosol of 4.5% saline delivered in a similar dose. This was particularly evident in Experiment 1 where there was a significantly lower dose of dry powder sodium chloride required to produce a 20% fall in FEV1 compared with the wet aerosol ($p<0.02$).

TABLE 1

EXPERIMENT 1

DRY POWDER SODIUM CHLORIDE VIA HALERMATIC

| Subject No | Medications | Steroids Dose (ug/day) | Duration (mth) | % Pred FEV1 Pre chall Control Day | 4.5% Saline PD20 (mg) | NaCl#1 PD20 (mg) | NaCl#2 PD20 (mg) |
|---|---|---|---|---|---|---|---|
| 1 | Fenoterol | | | 96.8 | 651.2 | 146 | 127 |
| 2 | Salbutamol | BUD 800 | 3 | 94.2 | 149.4 | 161 | 96 |
| 3 | Salbutamol | | | 119.7 | 295.2 | 155 | 162 |
| 4 | Salbutamol | | | 88.1 | 249.8 | 121 | 118 |
| 5 | Salbutamol | | | 110.3 | 508.5 | 423 | 588 |
| 6 | Salbutamol | | | 75.7 | 232.7 | 126 | 105 |
| 7 | Salbutamol | | | 106.2 | 153.0 | 20.45 | 75.69 |
| 8 | Salbutamol | | | 103.3 | 166.5 | 106 | 52 |
| 9 | Salbutamol | | | 80.1 | 79.7 | 29 | 40 |
| 10 | Terbutaline | BUD 1200 | 24 | 146.6 | 913.5 | 493.5 | 502.9 |
| 11 | Salbutamol | | | 86.4 | 725.4 | 36.1 | 79.5 |
| 12 | Salbutamol | BEC 500 | 4 | 122.4 | 515.3 | 340.7 | 268.6 |
| 13 | Terbutaline prn | BUD 800 | 6 | 81.5 | 205.7 | 257.99 | 128.8 |
| 14 | Salbutamol | BEC 1000 | 48 | 66.2 | 58.5 | 87.93 | 132.03 |
| 15 | Salbutamol | BUD 2000 | 23 | 76.3 | 16.7 | 19.4 | 62.9 |
| 16 | Salbutamol | | | 88.2 | 254.3 | 630 | 283.1 |
| 17 | Salbutamol | BEC 400 | 48 | 79.6 | 137.7 | 52.6 | 19.16 |
| | | | Mean | 95.4 | Geomean 215.23 | 116.3 | 116.8 |
| | | | SD | 20.6 | 95% CI [128.3,361.2] | [66.53,203.4] | [74.6,183.1] |
| | | | | | n = 17 | n = 17 | n = 17 |
| | | | | | | p = 0.02 | NS |
| | | | | | | n = 17 | n = 17 |

TABLE 2

EXPERIMENT 2

DRY POWDER MANNITOL VIA INGELHEIM INHALATOR

| Subj No. | Medications | Steroids Dose (ug/day) | Duration (mth) | % Pred FEV1 Pre chall Control day | 4.5% Saline PD20 (mg) | Mannitol #1 PD20 (mg) | Mannitol #2 PD20 (mg) | Mecholyl PD20 (umol) |
|---|---|---|---|---|---|---|---|---|
| 1 | Salbutamol | | | 100 | 296.1 | 92 | 102 | 3.12 |
| 2 | Salbutamol | BECL 400 | 72 | 102 | 32.85 | 61.7 | 43.1 | 0.27 |
| 3 | Fenoterol | BECL 1000 | 60 | 65.7 | 7.2 | 20.5 | 53 | 0.22 |
| 4 | Salbutamol | BUD 1600 | 24 | 65.5 | 163.35 | 131.2 | 183.2 | 1.04 |
| 5 | Salbutamol | BECL 100 | PRN | 92.6 | 955.8 | 112.2 | 96.9 | 0.79 |
| 6 | Salbutamol | BUD 2400 | 6 | 67.4 | 99.9 | 225 | | |
| 7 | Salbutamol | BEC 800 | 8 | 61.2 | 38.7 | 11.6 | 6.2 | |
| 8 | Terbutaline | BUD 1200 | 36 | 129 | 916.65 | 366 | 463.1 | 2.71 |
| 9 | Salbutamol | BUD 800 | 6 | 85.1 | 45.9 | 42.3 | 84.2 | 0.21 |
| 10 | Salbutamol | BUD 800 | 24 | 87.1 | 378 | 295 | 337.1 | 1.77 |
| 11 | Terb,Theo | BUD 6400 | 15 | 53.8 | 378 | >635 | >635 | |
| 12 | Salbutamol | | | 71.6 | 130.05 | 76 | 24.5 | |
| 13 | Salbutamol | BEC 500 | PRN | 116 | 229.95 | 77.5 | | |

TABLE 2-continued

EXPERIMENT 2

DRY POWDER MANNITOL VIA INGELHEIM INHALATOR

| Subj No. | Medications | Steroids Dose (ug/day) | Duration (mth) | % Pred FEV1 Pre chall Control day | | 4.5% Saline PD20 (mg) | Mannitol #1 PD20 (mg) | Mannitol #2 PD20 (mg) | Mecholyl PD20 (umol) |
|---|---|---|---|---|---|---|---|---|---|
| 14 | Salbutamol | | | 67.2 | | 363.15 | 113.9 | | |
| | | | | Mean 83.16 | Geomean | 149.4 | 85.84 | 77.99 | |
| | | | | SD 22.4 | CI | [67.7,329.8] | [47.8,156.9] | [31.57,192.67] | |
| | | | | | | n = 14 | n = 13 | n = 10 | |
| | | | | | | | NS | NS | |
| | | | | | | | n = 13 | n = 10 | |

TABLE 3

EXPERIMENT 3

DRY POWDER SODIUM CHLORIDE VIA INGELHEIM INHALATOR

| Subject No | Medications | Steroids Dose (ug/day) | Duration (mth) | % Pred FEV1 Pre chall Control Day | | 4.5% Saline PD20 (mg) | NaCl#1 PD20 (mg) | NaCl#2 PD20 (mg) |
|---|---|---|---|---|---|---|---|---|
| 1 | Salbutamol | | | 100 | | 296.1 | 73.7 | 172.1 |
| 2 | Salbutamol | BECL 400 | 72 | 102 | | 32.85 | 22.1 | 151 |
| 3 | Fenoterol | BECL 1000 | 60 | 65.7 | | 7.2 | 50.1 | 18.2 |
| 4 | Salbutamol | BUD 1600 | 24 | 65.5 | | 163.35 | 67.2 | 151 |
| 5 | Salbutamol | BECL 100 | PRN | 92.6 | | 955.8 | 107.7 | 103.8 |
| 6 | Salbutamol | BUD 2400 | 6 | 67.4 | | 99.9 | 168.2 | 138.22 |
| 7 | Terbutaline | BUD 1200 | 36 | 129 | | 916.65 | 407.2 | |
| 8 | Salbutamol | BUD 800 | 6 | 85.1 | | 45.9 | 105.6 | 55.08 |
| 9 | Salbutamol | BUD 800 | 24 | 87.1 | | 378 | 151.5 | 56.39 |
| 10 | Terb, Theo | BUD 6400 | 15 | 53.8 | | 378 | >635 | >635 |
| | | | | Mean 84.82 | Geomean | 152 | 95.3 | 86.67 |
| | | | | SD 22.5 | 95% CI | [49.7,464.7] | [50.6,179.43] | [50.6,183.6] |
| | | | | | | n = 10 | n = 9 | n = 8 |
| | | | | | | | NS | NS |
| | | | | | | | n = 9 | n = 8 |
| | | | | Mean | | p = 0.096 | | p = 0.69 |

SPONTANEOUS RECOVERY
Experiment No 3 dry sodium chloride through Inhalator
The mean ±SD value for $FEV_1$ expressed as a percentage of the pre-challenge pre-capsule value was 88.4%±10.6%, 30 minutes after challenge and 94.8%±7%, 60 mins after challenge.
TIME & NUMBER OF CAPSULES TAKEN for DRY CAPSULE CHALLENGE
For Experiment No 2
The mean time taken to perform the challenge with the dry capsule of mannitol was 10.0±3 min and varied from 6–14 minutes for the 13 subjects.
For Experiment No 3
The mean (±SD) time taken to perform the challenge with the dry capsule of sodium chloride was 10.6±3 min and varied from 6–15 minutes except in Subject 10 where it was 20 min. The mean number of capsules was 8.6±6.7 for subjects Nos 1–9. Subject 10 required 33 minutes but failed to respond. He was taking 6400 μg of Budesonide daily.
Inspiratory Flow Rates through the Halermatic
The inspiratory flow rates in all but a few inhalations exceeded 50 L/min. The flows became lower as the dose of powder in the capsule increased. Thus when the empty capsule was in the Halermatic the median flow was 96 L/min and when the 40 mg capsules were inhaled it was 73 L/min.
Inspiratory Flow rates through the Inhalator
These were only measured once on each day of study. In all subjects the flow rate exceeded 43 L/min and the range was 43–70 L/min median value was 57 L/min.

Oxygen Saturation during challenge
An Ohmeda Biox pulse oximeter (3700e Louisville, Colo. USA) was used to measure arterial oxygen saturation. This was performed as an index of safety to ensure that severe hypoxemia did not occur during the inhalation of mannitol. Only three subjects had a reduction in saturation of greater than 3% and all values for saturation remained within the normal range throughout the challenges with dry powders.
Healthy Control Subjects
Five healthy control subjects (aged 19–22 yr) were studied, four received a dose of 620 mg and one 540 mg. None of these healthy volunteers, who acted as control subjects, recorded a $PD_{20}$ and the maximum % fall in $FEV_1$ was 6.5% with the range being 0–6.5%.
DISCUSSION
The results of this study clearly demonstrate that both sodium chloride and mannitol, delivered from a capsule via either a Halermatic or Inhalator device, can provoke airway narrowing in the same asthmatic subjects who are sensitive to the wet aerosol preparation of saline. There was a good range in the severity of the hyperresponsiveness of asthma as demonstrated by the $PD_{20}$ to the wet aerosol. There were no adverse experiences requiring medical intervention. The mannitol powder was extremely well tolerated. Some subjects found difficulty in inhaling the powder of sodium chloride, particularly in the 40 mg dose. We estimated that less than 30% of the dose deposited in the lower respiratory tract while the remainder impacted on the device and the throat. Ideally a greater percentage of the dose would have a particle size in the respirable range.

The advantages of the dry powder challenge over the wet aerosol challenge include; the faster time for challenge, the reduced necessity to clean apparatus and the potentially disposable nature of the inhalers.

This is the first ever report of the effect of inhalation of a dry powder of mannitol in human airways. This is the first report of the airway narrowing effects of dry particles of sodium chloride in known asthmatic subjects.

The only reference to inhalation of particles of sodium chloride in the respirable range is as a treatment for children suffering from bronchial asthma. Tikhomirov, Povlotska,& Zmievskaya (CC Number SU 1581325, Kind A Date 900730 Week 9113 (Basic) from the Soviet Union have reported that a course of 10–15 daily inhalations of a NaCl aerosol (containing 70–80% of 3 micron particles with a density of 9–12 mg/cubic meter) given in a chamber with air velocity of 0.1–0.2 m/sec, 40–60 vol % of relative humidity at 16–18 degrees for periods gradually increasing from 6–15 min would increase remission of asthma of up to 1 year in 61.5% of cases. The concentration of dry powder particles in our application is much higher, being typically between 2.5–10 mg/liter (250–1620 mg/cubic meter), and the application for our study is acute airway narrowing for diagnostic purposes not treatment.

METHODS AND RESULTS FOR THE NASAL CHALLENGE

This study was performed on a single subject. The subject was familiar with the methods and could perform reproducible results. The subject voluntarily activated his alar nasae muscles to prevent nasal airway narrowing on inspiration, and breathed at normal tidal volume and rate with peak inspiratory flow of at least 0.5 L/sec. The studies were performed in a seated position in an air conditioned room with ambient temperature controlled between 21.5° and 23.5° C. and relative humidity between 55 and 65%.

Transnasal pressure and flow were measured by posterior rhinomanometry. Flow was measured using a modified Sullivan mask (Rescare, Australia) attached to a No.2 Fleish pneumotachygraph. A firm air filled catheter was placed on the posterior tongue and sealed with the lips. This was referenced to the mask pressure and changes were measured with a Validyne MP45 pressure transducer (Validyne Corp, Northbridge, Calif.). Pressure and flow signals were recorded at a rate of 12 Hertz and were plotted simultaneously on a computer screen.

The pressure/flow data from a sample of between 5 and 7 breaths was recorded. Rohrer's equation (pressure drop= $k_1*flow+k_2*flow_2$) was fitted to the data by least squares multiple linear regression. The nominal nasal resistance was then calculated from the fitted pressure drop at a flow rate of 0.5 L/sec in the inspiratory direction. Baseline nasal resistance was the average of at least 4 measurements. Once the baseline was established subjects underwent the challenge protocol and nasal resistance was measured at 1, 2, 4, 6, 8, 10, 15, and 20 minutes after the challenge.

The salt was delivered to the nasal mucosa using a Spinhaler device (Fisons Pharmaceuticals)loaded with half the total dose. The subject placed the loaded Spinhaler just inside one nostril and inhaled deeply. If the salt capsule was not empty after one inhalation, the subject performed another until the capsule was completely empty. The device was then reloaded and the other nostril was used.

Figure 3:
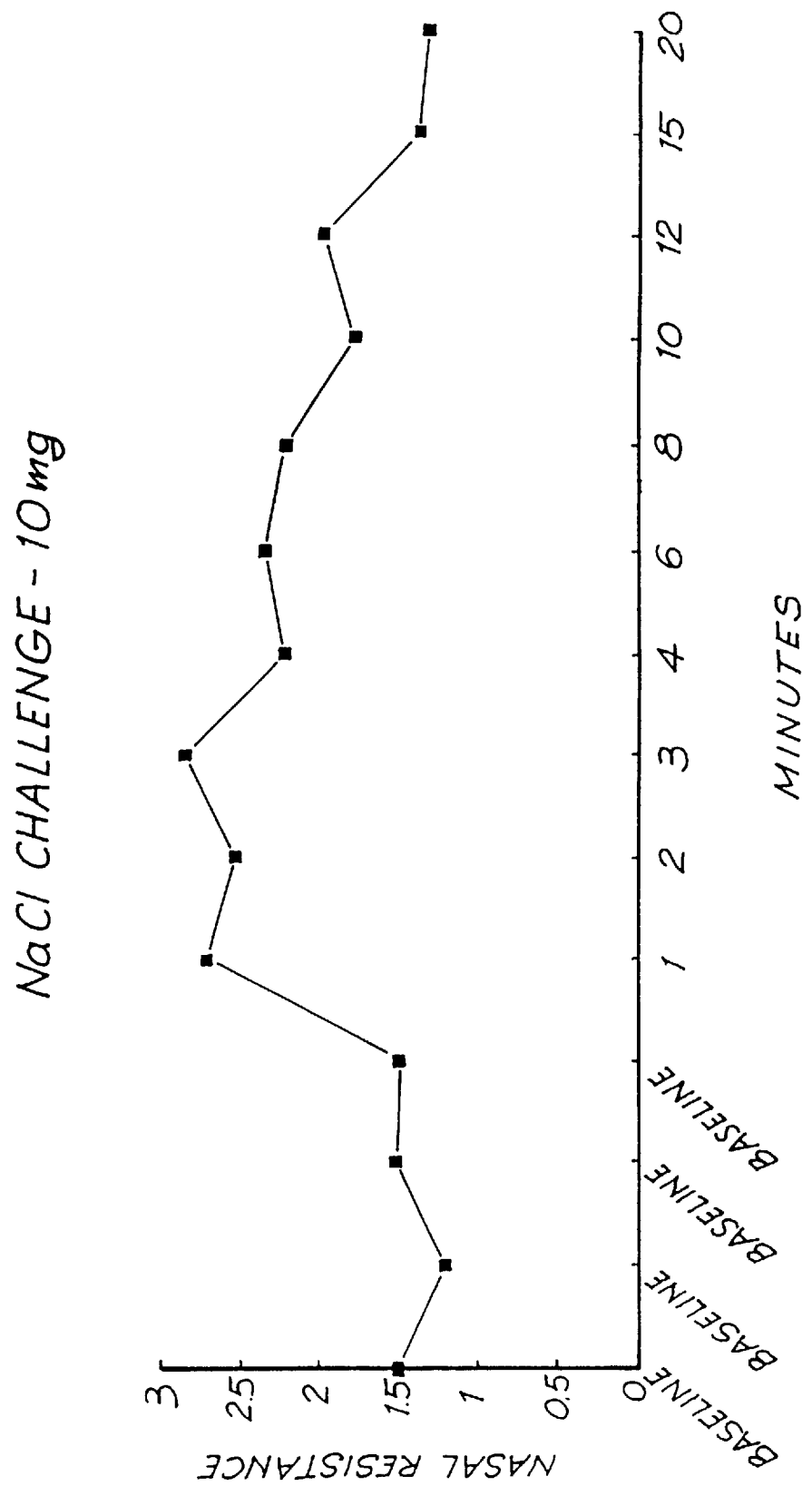
FIG. 3 is a graph showing nasal airflow resistance before and after a dry powder challenge according to the present invention.
Figure 4:
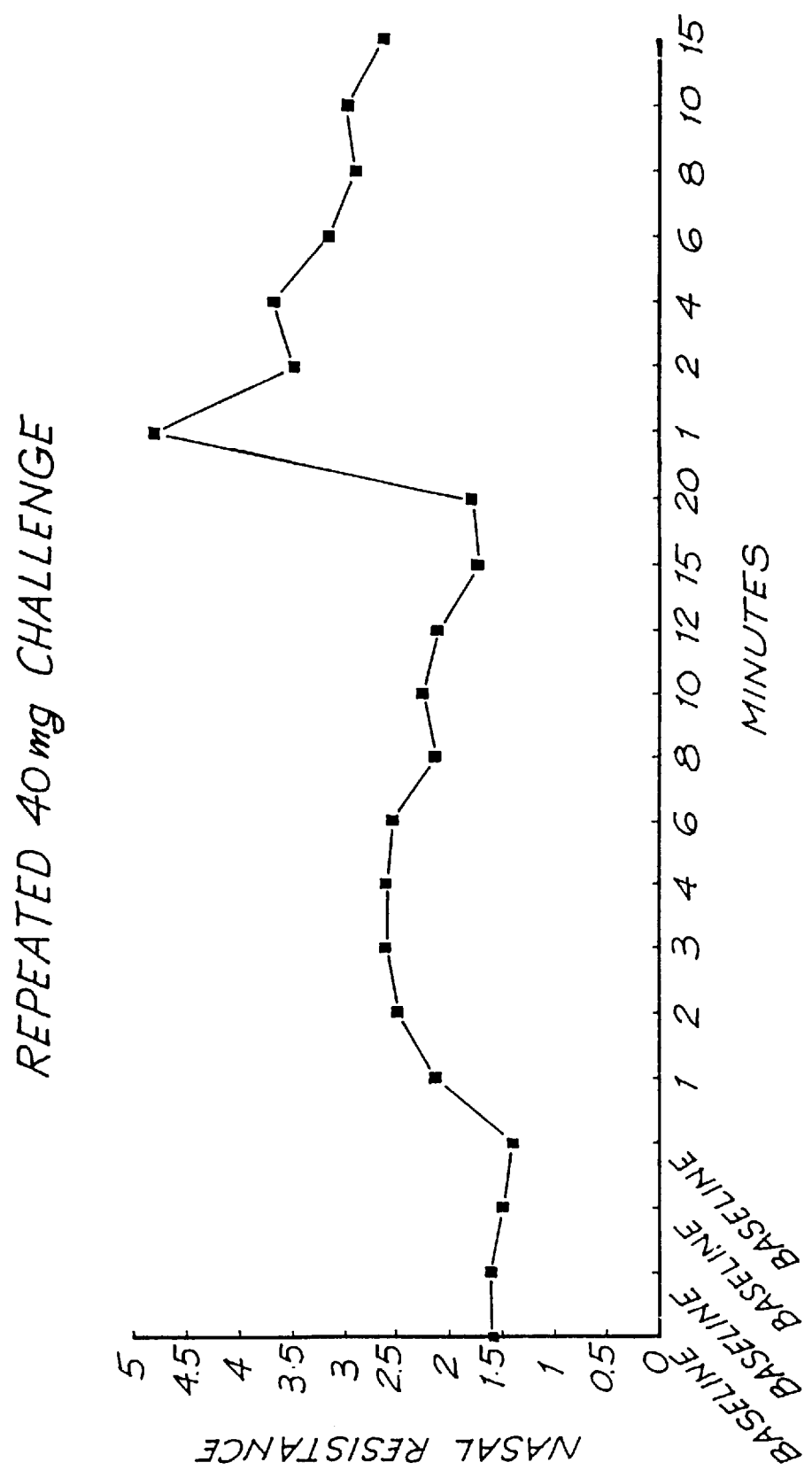
FIG. 4 is a graph showing nasal airflow resistance before and after two successive dry powder challenges according to the present invention.

The FIGS. 3 & 4 show nasal resistance over 4 baseline measurements before challenge, followed by measurements made after the challenge. Nasal resistance is expressed as cm $H_2O/L/sec$. Both illustrate an increase in nasal resistance at 1 minute with a gradual fall to baseline over 15 minutes. This pattern is very similar to that seen with cold dry air both in terms of the degree of increase and the pattern of the subsequent fall to baseline. FIG. 4 shows results following inhalation of 40 mg, measurements for 20 minutes then a repeat dose of 40 mg.

Method for measuring mucociliary clearance Mucociliary clearance is assessed using a radioaerosol technique (99 mTc-sulphur colloid is commonly used). The radioaerosol should be generated with a nebuliser that produces droplets that have a mass median aerodynamic diameter (MMAD) of about 6 mm and a geometric standard deviation (GSD) under 2. A monodisperse aerosol would be ideal. The radioaerosol should be delivered with a controlled breathing pattern to achieve deposition in the large airways or the conducting airways. This is best achieved by having a target, on a computer or an oscilloscope screen, that sets the tidal volume and the inspiratory and expiratory times. Experimental data have shown that a tidal volume of 450 ml and a peak inspiratory flow rate of about 60 L/min is a good breathing pattern for central deposition. The activity delivered in the lungs should be about 40 MBq, so the delivery time should be adjusted accordingly. Usually 2 to 3 minutes is sufficient if the starting activity in the nebuliser is about 1 GBq.

Measurement of mucociliary clearance should start as soon as possible after the delivery of the radioaerosol. The best way to assess mucociliary clearance is using a gamma camera. Collection of emission images with a gamma camera gives good information about the initial deposition of radioaerosol in terms of distribution and intensity. Serial anterior/posterior images for about one hour provide the best data for assessing mucociliary clearance. A big advantage is that a regional analysis can be achieved for assessing mucociliary clearance of the large and small airways. Mucociliary clearance follows, usually, a bi-exponential pattern and curve fitting is commonly used to smooth the data. The salt or mannitol is administered after the collection of the first images that are used to assess the initial deposition of the radioaerosol.

CONCLUSION

Dry powders of substances that have the potential to increase the osmolarity of the airway surface liquid, when inhaled in an adequate dose containing an adequate amount of respirable particles are suitable for use in bronchial provocation testing to identify persons with airway hyper-responsiveness consistent with asthma. These same substances can also be inhaled into the nose to identify persons with rhinitis. These same substances have the potential to be used to induce sputum and increase mucociliary clearance.

I claim:

1. A method for attempting to provoke airway narrowing in a subject comprising the steps of (a) causing the subject to inhale into subject's airways an effective amount of a substance capable of increasing the osmolarity of airway surface liquid in the subject, which substance is in the form of a dry dispersable powder, other than a dry powder dissolved in a liquid, containing an effective proportion of particles of a respirable size, and (b) measuring in the subject a parameter indicative of the resistance to air flow of the subject's airway.

2. A method as claimed in claim 1 in which the subject is caused to inhale the substance into the airways of a lung.

3. A method as claimed in claim 1 in which the subject is caused to inhale the substance into a nasal airway.

4. A method as claimed in claim 1 in which the substance is selected from the group comprising mineral salts, sugars and sugar alcohols.

5. A method as claimed in claim 4 in which the substance is selected from the group comprising salts of sodium or potassium, hexose and pentose sugars and their corresponding sugar alcohols.

6. A method as claimed in claim 5 in which the substance is selected from the group comprising sodium chloride, potassium chloride, mannitol and dextrose.

7. A method as claimed in claim 1 in which an effective quantity of the dry particles have a maximum dimension of seven microns.

8. A method as claimed in claim 1 in which the proportion of the particles having a respirable size is at least 10% by weight of the substance, preferably at least 25%, more preferably at least 40% and most preferably at least 50%.

9. A method as claimed in claim 1 in which the parameter indicative of airway narrowing that is measured comprises measuring a reduction in forced expiratory volume in one second.

10. A method as claimed in claim 1 in which the substance is packaged in a rupturable hard capsule.

11. A method as claimed in claim 10 in which the capsule contains from 1 to 100 mg of the substance, preferably 5 to 40 mg.

12. A method for increasing mucociliary clearance or inducing sputum comprising the step of causing a subject to inhale into the subject's airways an effective amount of a substance capable of increasing the osmolarity of airway surface liquid, the substance being in the form of a dispersible dry powder, other than a dry powder dissolved in a liquid, containing an effective proportion of particles of a respirable size.

13. A method as claimed in claim 12 in which the subject is caused to inhale the substance into the airways of a lung.

14. A method as claimed in claim 12 in which the subject is caused to inhale the substance into a nasal airway.

15. A method as claimed in claim 12 in which the substance is selected from the group comprising mineral salts, sugars and sugar alcohols.

16. A method as claimed in claim 15 in which the substance is selected from the group comprising salts of sodium or potassium, hexose and pentose sugars and their corresponding sugar alcohols.

17. A method as claimed in claim 16 in which the substance is selected from the group comprising sodium chloride, potassium chloride, mannitol and dextrose.

18. A method as claimed in claim 12 in which an effective quantity of the dry particles have a maximum dimension of seven microns.

19. A method as claimed in claim 12 in which the proportion of the particles having a respirable size is at least 10% by weight of the substance, preferably at least 25%, more preferably at least 40% and most preferably at least 50%.

20. A method as claimed in claim 12 in which the substance is packaged in a rupturable hard capsule.

21. A method as claimed in claim 20 in which the capsule contains from 1 to 100 mg of the substance, preferably 5 to 40 mg.

* * * * *

UNITED STATES PATENT AND TRADEMARK OFFICE
CERTIFICATE OF CORRECTION

PATENT NO.: 5,817,028
DATED : October 6, 1998
INVENTOR(S): Sandra Doreen Anderson It is hereby certified that error appear(s) in the above-identified patent and that said Letters Patent is hereby corrected as shown below:

Abstract, line10, please delete "rhinitus" and insert --rhinitis--

Col. 6, line 28; please delete "13-6.8 mm, 6.8-3.1 mm" and insert --13-6.8 µm, 6.8-3.1 µm--

Col. 6, line 29; please delete "mm" and insert --µm--

Col. 11, line 53; please delete "$k_1 *flow + k_2 *flow_2$" and insert --$k_1 *flow + k_2 *flow^2$--

Col. 12, line 16; please delete "mm" and insert --µm--

Signed and Sealed this

Twenty-fourth Day of August, 1999

Attest:

Q. TODD DICKINSON

Attesting Officer     Acting Commissioner of Patents and Trademarks